United States Patent
Corey, Jr.

[11] Patent Number: 6,117,390
[45] Date of Patent: Sep. 12, 2000

[54] COMPACT BLOOD OXYGENATOR UTILIZING LONGITUDINALLY INTERSPERSED TRANSVERSELY EXTENDING HEAT EXCHANGER CONDUITS AND OXYGENATOR FIBERS

[75] Inventor: Edmund R. Corey, Jr., Brewster, Mass.

[73] Assignee: Medtronic, Inc., Minneapolis, Minn.

[21] Appl. No.: 09/049,413

[22] Filed: Mar. 27, 1998

[51] Int. Cl.$^7$ .................................................. A61M 1/14
[52] U.S. Cl. ................................ 422/45; 422/44; 422/48
[58] Field of Search ...................... 422/44, 45, 46

[56] References Cited

U.S. PATENT DOCUMENTS

| | | | |
|---|---|---|---|
| 3,839,204 | 10/1974 | Ingenito et al. | 210/181 |
| 4,256,692 | 3/1981 | Cover | 422/46 |
| 4,636,309 | 1/1987 | Bellhouse | 210/321.3 |
| 4,791,054 | 12/1988 | Hamada et al. | 435/2 |
| 4,876,066 | 10/1989 | Bringham et al. | 422/46 |
| 4,902,476 | 2/1990 | Gordon et al. | 422/46 |
| 4,917,797 | 4/1990 | Inacio et al. | 210/184 |
| 4,940,617 | 7/1990 | Baumeister | 427/36.3 |
| 5,043,140 | 8/1991 | Combs | 422/46 |
| 5,137,531 | 8/1992 | Lee et al. | 422/46 |
| 5,188,801 | 2/1993 | Fini | 422/48 |
| 5,211,546 | 5/1993 | Isaacson | 417/356 |
| 5,224,522 | 7/1993 | Baurmeister | 139/431 |
| 5,263,924 | 11/1993 | Mathewson | 604/4 |
| 5,266,265 | 11/1993 | Raible | 422/64 |
| 5,270,005 | 12/1993 | Raible | 422/46 |
| 5,290,236 | 3/1994 | Mathewson | 604/131 |
| 5,297,591 | 3/1994 | Baurmeister | 139/383 |
| 5,312,589 | 5/1994 | Reeder et al. | 422/45 |
| 5,429,184 | 7/1995 | Bach et al. | 165/149 |
| 5,634,892 | 6/1997 | Whalen | 604/4 |
| 5,718,869 | 2/1998 | Bach et al. | 422/45 |
| 5,747,138 | 5/1998 | Leonard | 428/113 |
| 5,762,868 | 6/1998 | Leonard | 422/46 |

FOREIGN PATENT DOCUMENTS

| | | | |
|---|---|---|---|
| 050722 | 3/1992 | European Pat. Off. | 422/44 |
| 04180771 | 11/1990 | Japan | A61M 1/14 |
| WO 89/00864 | 2/1989 | WIPO | A61M 1/18 |

*Primary Examiner*—Corrine McDermott
*Assistant Examiner*—Cheryl L. Huseman
*Attorney, Agent, or Firm*—Harold R. Patton; Michael J. Jaro

[57] ABSTRACT

A compact blood oxygenator has a minimal priming volume and is particularly advantageous for pediatric cardiac surgery. A generally rectangular housing has longitudinally spaced and interspersed heat exchanger conduit groups and oxygenator fiber bundles. The conduits and oxygenator fibers extend transversely across the interior of the housing in criss-cross fashion. Cured potting compound and flanges on the interior surfaces of the housing define hermetically sealed heat transfer fluid, blood and gas mixture flow paths. The inlet and outlet ends of the heat exchanger conduits communicate with first and second chambers formed on opposite sides of the housing. The inlet and outlet ends of the oxygenator fibers communicate with third and fourth chambers on the other opposite sides of the housing. The potting compound is formed into a rectangular block with an interior wall that defines a longitudinally extending one-way cylindrical blood flow path that minimizes eddies and stagnant areas that can cause platelet damage or clotting. The oxygenator fiber bundles are made of a fan folded mat of a plurality of generally parallel oxygenator fibers. An axial flow pump is mounted adjacent a blood inlet manifold in the upper end of the housing. The blood oxygenator may be connected to the patient as part of a perfusion circuit which has an accumulator reservoir to minimize tissue damage to the patient.

19 Claims, 6 Drawing Sheets

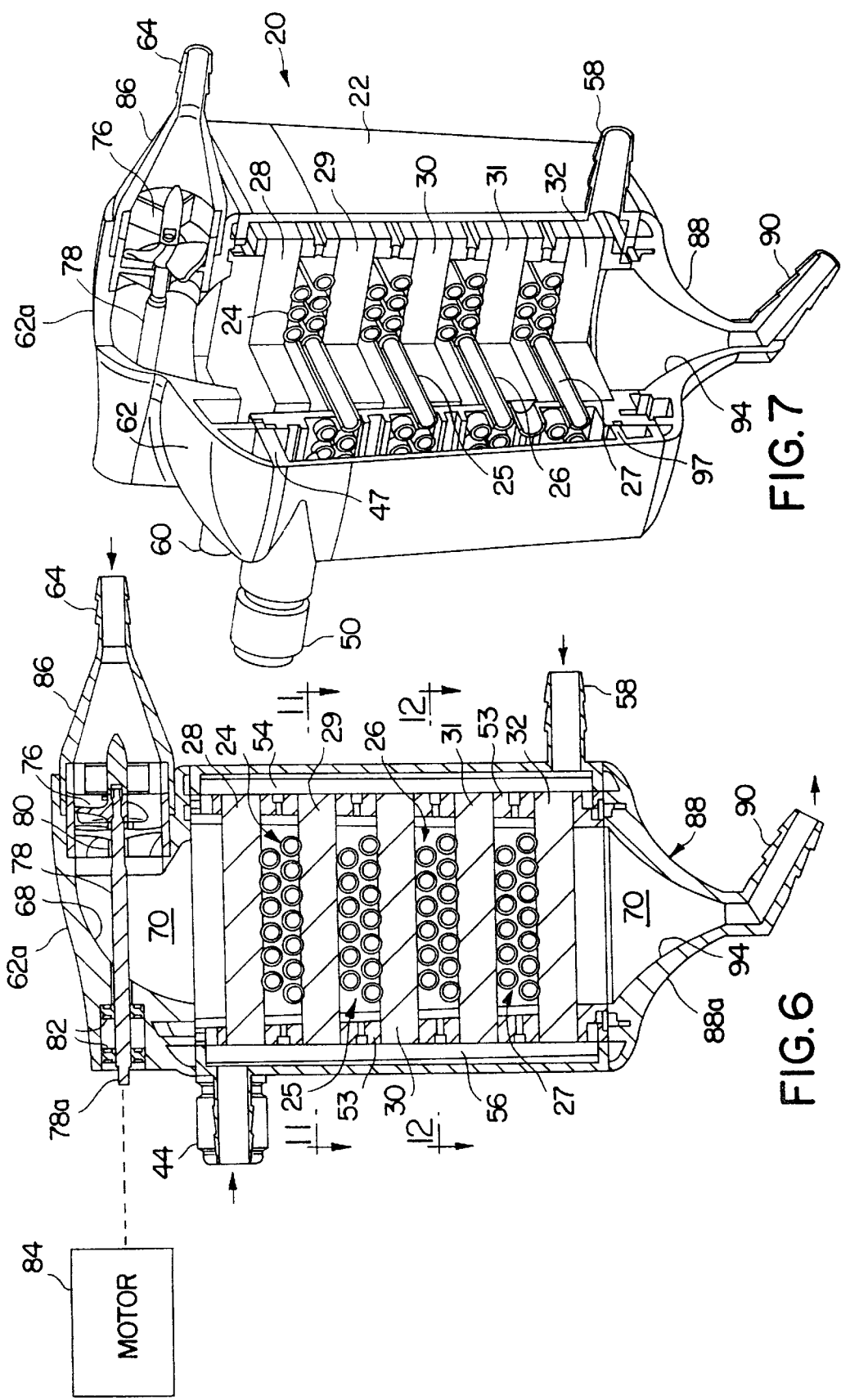

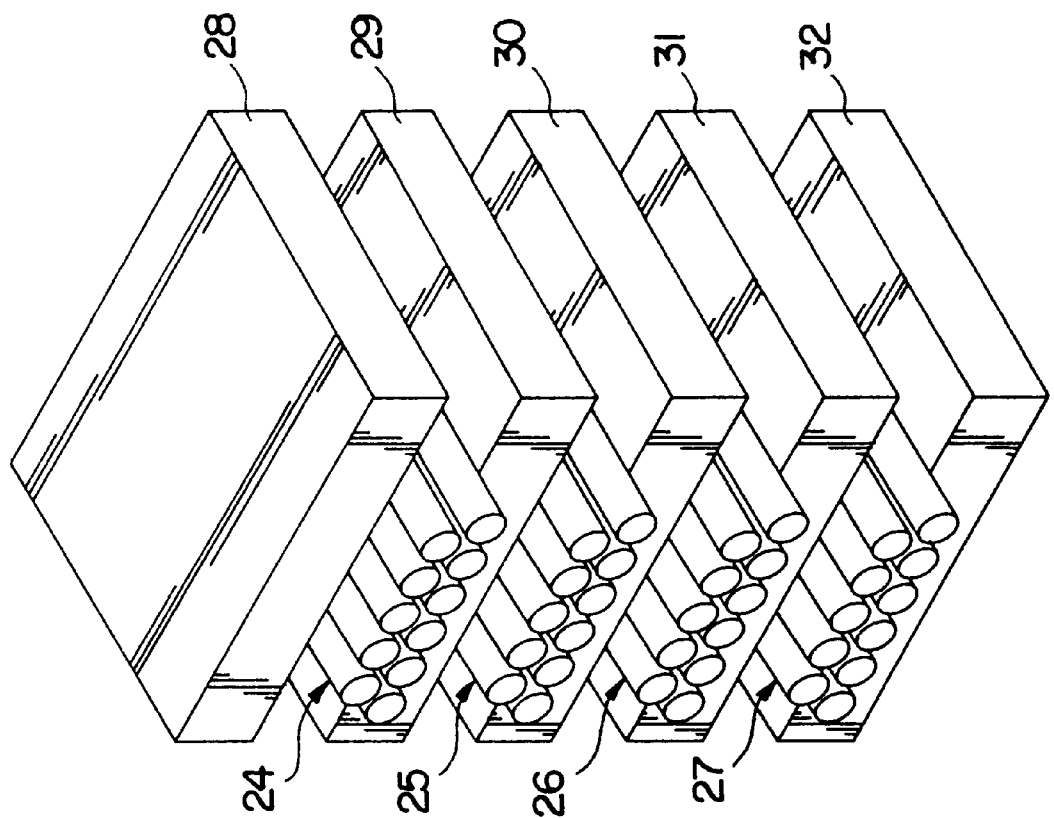
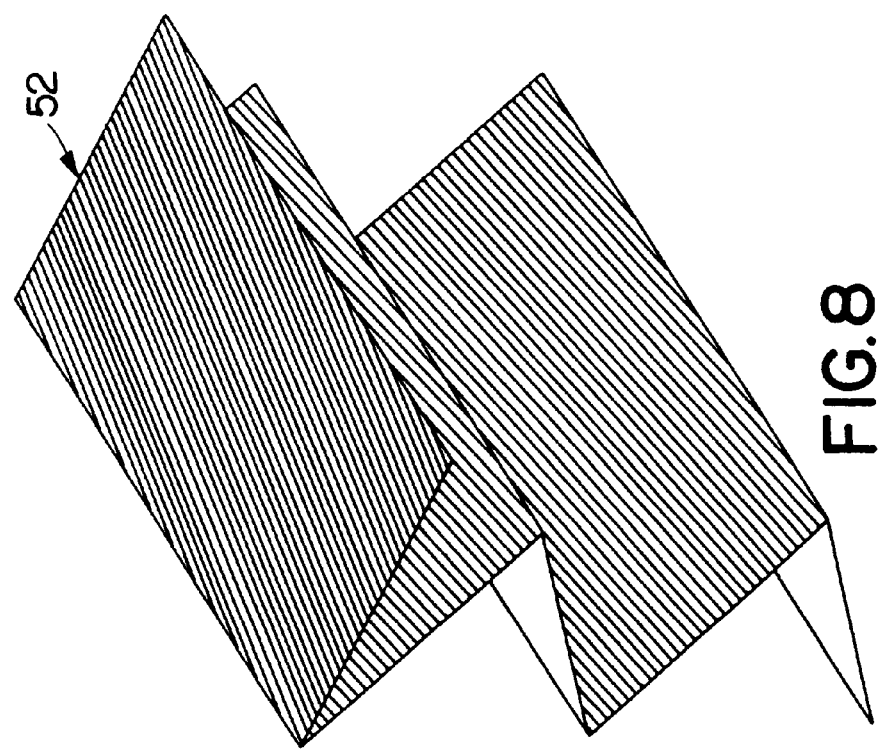

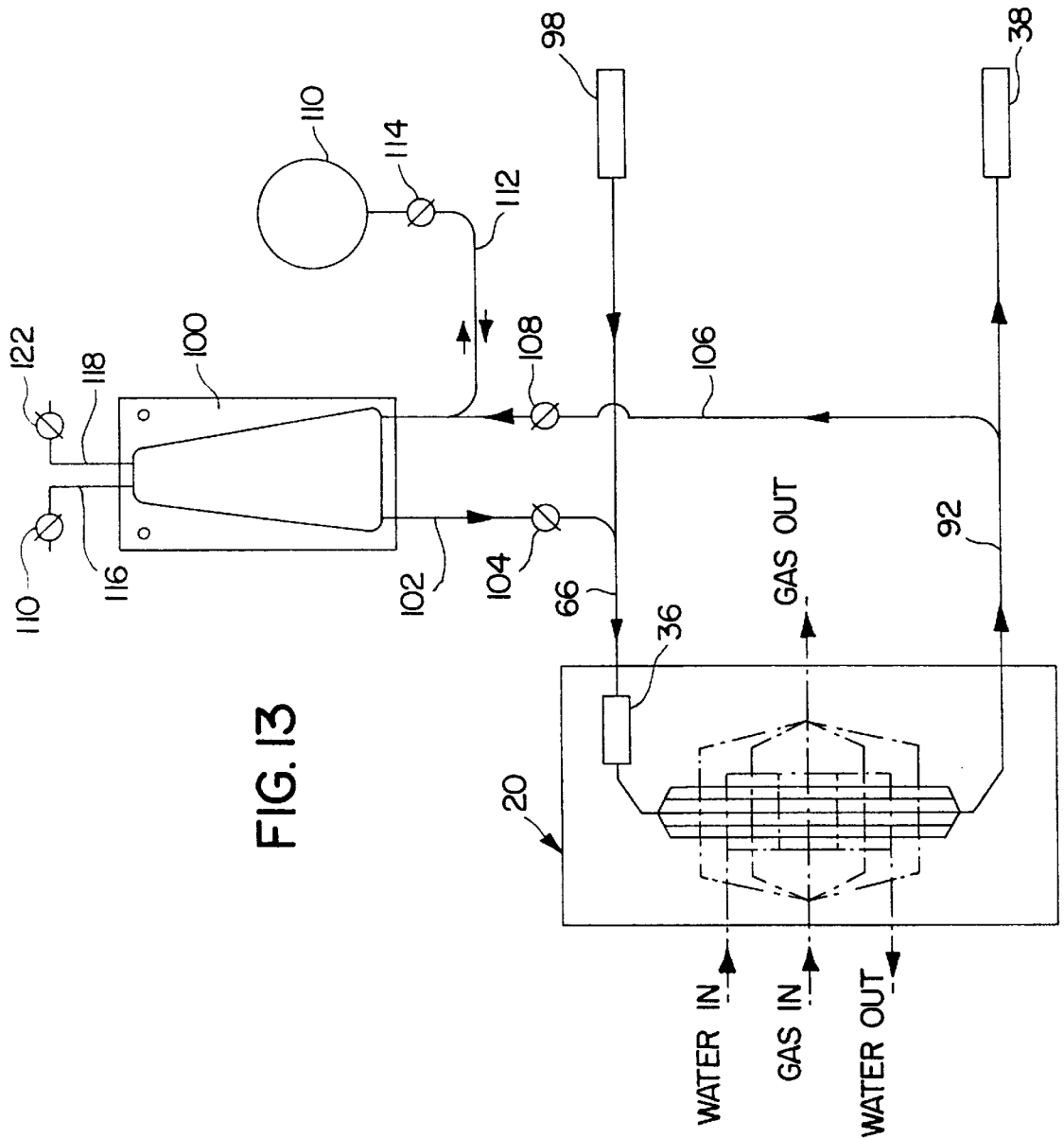

COMPACT BLOOD OXYGENATOR UTILIZING LONGITUDINALLY INTERSPERSED TRANSVERSELY EXTENDING HEAT EXCHANGER CONDUITS AND OXYGENATOR FIBERS

BACKGROUND OF THE INVENTION

The present invention relates to surgical support apparatus, and more particularly, to an improved blood oxygenator and modified perfusion circuit used to maintain a patient's blood at a predetermined temperature while replacing carbon dioxide in the blood with oxygen.

Blood oxygenators are well known in the medical field. Usually they are disposable components of so-called "heart-lung machines." These machines mechanically pump a patient's blood and oxygenate the blood during major surgery such as a heart bypass operation. A typical commercially available blood oxygenator includes a heat exchanger and a membrane-type oxygenator. The patient's blood is continuously pumped through the heat exchanger. A suitable heat transfer fluid such as water is also pumped through the heat exchanger, separated from the blood but in heat transfer relationship therewith. The water is either heated or cooled externally of the blood oxygenator to maintain the patient's blood at a predetermined desired temperature. The membrane oxygenator comprises a so-called "bundle" of thousands of tiny hollow fibers made of a special polymer material having microscopic pores. Blood exiting the heat exchanger flows around the outside surfaces of these fibers. At the same time an oxygen-rich gas mixture sometimes including anesthetic agents, flows through the hollow fibers. Due to the relatively high concentration of carbon dioxide in the blood arriving from the patient, carbon dioxide from the blood diffuses through the microscopic pores in the fibers and into the gas mixture. Due to the relatively low concentration of oxygen in the blood arriving from the patient, oxygen from the gas mixture diffuses through the microscopic pores in the fibers into the blood. The oxygen content of the blood is raised, and its carbon dioxide content is reduced. The blood is also heated or cooled before being returned to the patient.

A blood oxygenator must have a sufficient volumetric flow rate to allow proper temperature control and oxygenation. However, blood is typically in short supply and is very expensive. Therefore, it is desirable to minimize the volume of blood contained within the oxygenator, preferably to less than five hundred cubic centimeters for adults and preferably less than one hundred and fifty cubic centimeters for infants. However, it is necessary to provide three separate flow paths for the heat transfer fluid, blood and the gas mixture. These separate flow paths must be hermetically sealed relative to each other and to the ambient environment. At the same time, the three fluids need to be in close proximity to one another in order to interact to regulate the blood temperature and perform the artificial lung function. This leads to complex and relatively large structures having significant blood priming volumes.

The cells and platelets in human blood are delicate and can be traumatized if subjected to excessive shear forces. Therefore, the blood flow velocity inside a blood oxygenator must not be excessive. In addition, the configuration and geometry of the blood flow path for a given blood flow rate must not create re-circulations (eddies) or stagnant areas that can lead to clotting. Many prior art blood oxygenators have tortuous blood flow paths characterized by sharp turns.

The foregoing design objectives must be met with a view towards making the blood oxygenator as inexpensive as possible. Since it is impractical to sterilize a blood oxygenator for re-use it must be discarded after a single surgery. The materials from which a blood oxygenator is fabricated must be approved by the Food and Drug Administration (FDA) of the U.S. Government for human surgical usage in the United States.

SUMMARY OF THE INVENTION

It is therefore the primary object of the present invention to provide an improved blood oxygenator.

It is another object of the present invention to minimize the internal volume of a blood oxygenator that must be filled with blood.

It is another object of the present invention to provide a blood oxygenator with an improved blood flow path designed to minimnize trauma to blood cells and platelets.

It is another object of the present invention to provide a blood oxygenator with an improved blood flow path designed to minimize re-circulations and stagnant areas that could lead to clotting.

It is still another object of the present invention to provide an improved perfusion circuit for oxygenating a patient's blood during cardiac surgery.

In accordance with the present invention a compact blood oxygenator comprises a housing defining a hollow interior, longitudinally interspersed heat exchanger conduits and oxygenator fibers extending in a transverse direction across the interior of the housing in criss-cross fashion, and hermetic seals between a plurality of ends of the heat exchanger conduits, a plurality of ends of the oxygenator fibers and a plurality of inner surfaces of the housing to define a transverse heat transfer fluid flow path extending through the heat exchanger conduits, a longitudinal blood flow path extending around the heat exchanger conduits and the oxygenator fibers, and a transverse gas mixture flow path extending through the oxygenator fibers.

BRIEF DESCRIPTION OF THE DRAWINGS

The following drawing figures illustrate a preferred embodiment of the present invention. Throughout the drawing figures, like reference numerals refer to like parts.

FIG. 6 is an enlarged vertical sectional view of the blood oxygenator of FIG. 1 taken along line 6—6 of FIG. 2.

FIG. 7 is an enlarged isometric view of the blood oxygenator of FIG. 1 with one quarter section broken away.

FIG. 8 is a greatly enlarged isometric view of a fan folded segment of a mat of oxygenator fibers illustrating the construction of one of the oxygenator fiber bundles of the blood oxygenator of FIG. 1.

FIG. 9 is a greatly enlarged isometric view illustrating the vertically interspersed discrete heat exchanger conduit groups and discrete oxygenator fiber bundles of the blood oxygenator of FIG. 1.

FIG. 13 is a schematic diagram of a specially modified perfusion circuit incorporating the blood oxygenator of FIG. 1.

DETAILED DESCRIPTION OF THE PREFERRED EMBODIMENT

Figure 1:
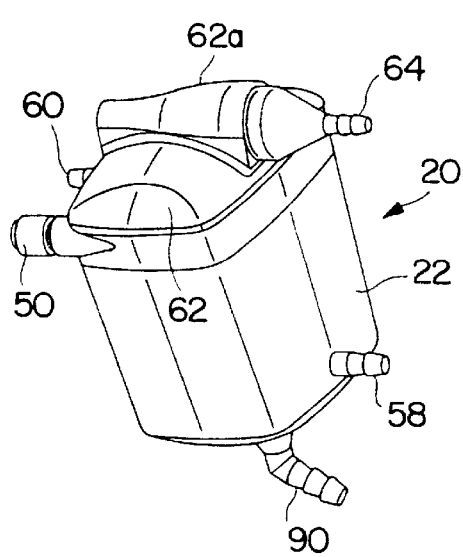
FIG. 1 is an isometric view of a blood oxygenator constructed in accordance with the present invention.
Figure 10:
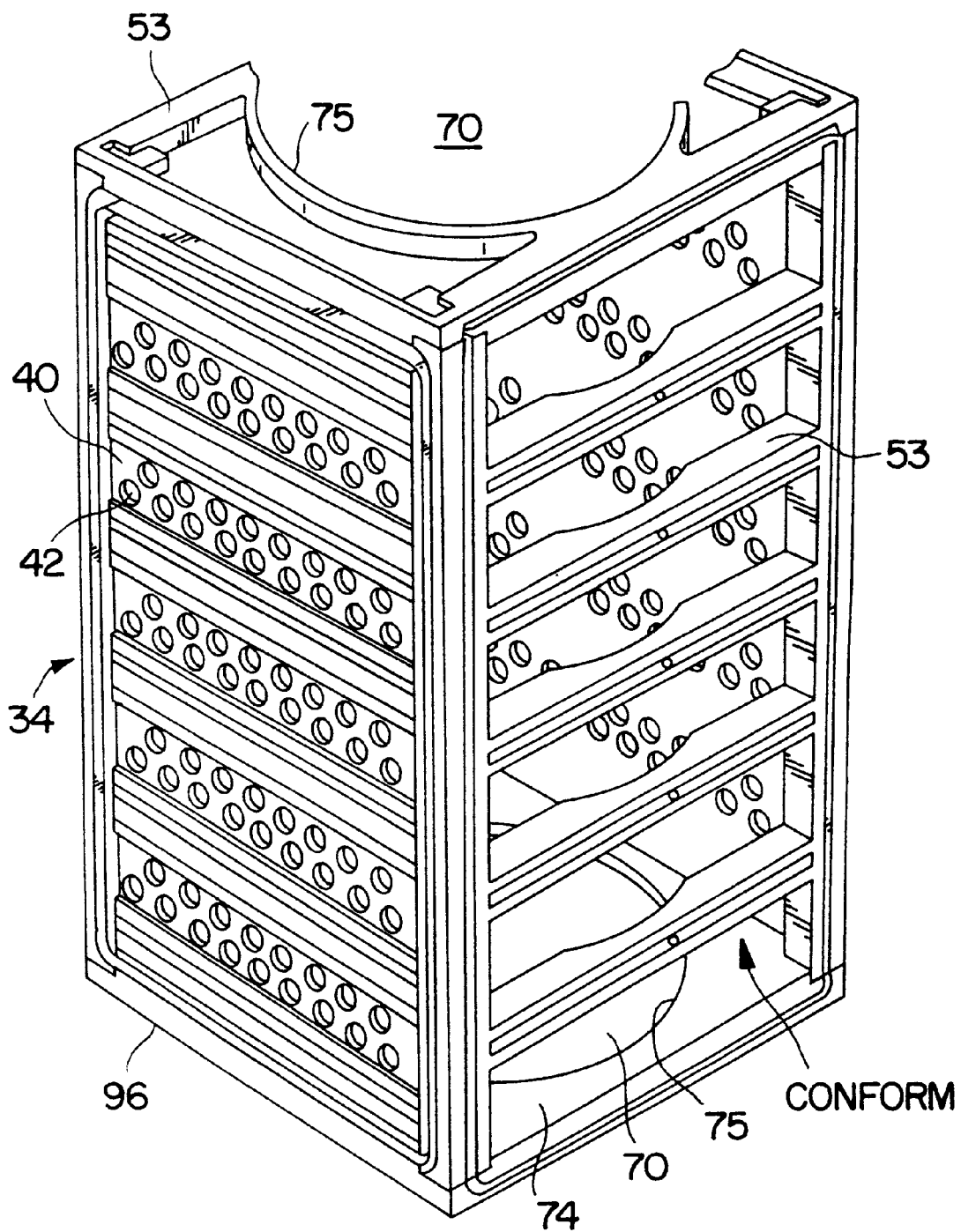
FIG. 10 is an enlarged isometric view of a rectangular skeletal framework that supports the conduit groups and oxygenator fiber bundles within the interior of the blood oxygenator of FIG. 1. A portion of the framework is broken away at the top thereof.

Referring to FIGS. 1 and 6, a compact blood oxygenator 20 constructed in accordance with the preferred embodiment of the present invention includes a generally rectangular vertically extending housing 22 defining a hollow interior. Within the hollow interior are four longitudinally spaced discrete heat exchanger conduit groups 24, 25, 26 and 27 and five longitudinally spaced discrete oxygenator fiber bundles 28, 29, 30, 31 and 32. The conduit groups 24–27 and fiber bundles 28–32 are vertically interspersed as best seen in FIG. 9 and are supported within the housing 22 by a generally rectangular vertically extending skeletal framework 34 (FIG. 10). The conduit groups 24–27 and the fiber bundles 28–32 are each formed of a plurality of individual conduits and fibers, respectively, that extend in a transverse direction across the interior of the housing 22 in criss-cross fashion. A heat transfer fluid flow path has a transverse segment that extends through the heat exchanger conduits. Sterile water is preferably used as the heat transfer fluid to minimize any risks to the patient should there be any minor leakage into the blood flow path. A longitudinal blood flow path extends downwardly around the exterior of the heat exchanger conduits and the exterior of the oxygenator fibers. A gas mixture flow path has a transverse segment that extends through the hollow interiors of the oxygenator fibers. As hereafter described in detail, the three flow paths are hermetically sealed relative to each other and relative to the ambient environment to prevent contamination. At the same time they are interleaved in an extremely efficient manner to permit the required blood temperature control and oxygenation functions while minimizing the priming volume of the blood oxygenator 20 and virtually eliminating any eddies or stagnant blood flow areas that could damage blood cells or lead to clotting.

FIG. 13 illustrates the heat transfer fluid flow path diagrammatically through the blood oxygenator 20 with the arrows labeled WATER IN and WATER OUT and the dashed lines connecting these arrows. Similarly the gas mixture flow path is illustrated diagrammatically in FIG. 13 with the arrows labeled GAS IN and GAS OUT and the dashed lines connecting these arrows. Finally, the blood flow path is illustrated in FIG. 13 by the solid lines extending vertically through the blood oxygenator 20 from a pump 36 to an inlet cannula 38 implanted in a clinically appropriate vessel of the patient such as an artery. The blood flows into the pump 36, which is mounted within the top of the blood oxygenator 20, and out of the bottom of the blood oxygenator 20 to the inlet cannula 38 in the direction indicated by the arrow heads.

The heat exchanger conduit groups 24–27 (FIG. 9) collectively define a heat exchanger. Each group such as 27 includes two tightly packed generally planar horizontal rows of parallel conduits in the form of metal tubes 27a. The lower row has seven tubes and the upper row has six tubes. The thirteen tubes 27a have an equal overall length dimensioned to extend across a majority of the interior of the housing 22. As seen in FIG. 7, the tubes 27a terminate short of the interior surfaces of the housing 22. The tubes 27a may be made of thin walled stainless steel or Aluminum and may have an internal diameter of one-quarter inch, for example. The number, size, shape and wall thickness of the tubes 27a is selected to ensure optimum heat transfer efficiency between the water inside the tubes and the patient's blood flowing around the outside of the tubes. The conduits need not be round in cross-section and they may be made of plastic or other suitable materials. The skeletal framework 34 (FIG. 10) has vertical side walls 40 formed with holes 42 for snugly receiving the ends of each of the tubes of each of the conduit groups 24–27.

Figure 12:
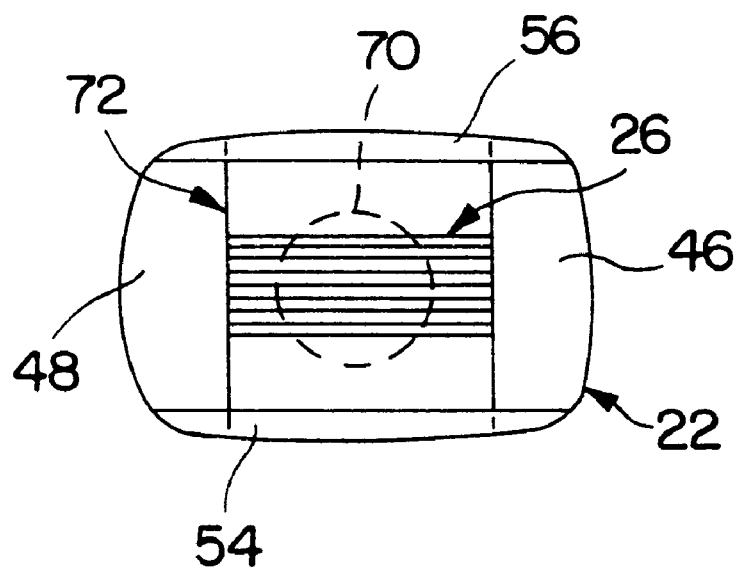
FIG. 12 is a diagrammatic horizontal cross-sectional view of the blood oxygenator of FIG. 1 taken along line 12—12 of FIG. 6.

Water from a source is pumped through a hose (not illustrated) connected to an inlet fitting 44 (FIG. 2) coupled to the housing 22 into a water entry chamber 46 (FIG. 12) formed inside the housing 22 on a first side thereof. The chamber 46 communicates with a first set of ends of all of the conduits of the groups 24–27. The water flows through the conduits and exits a second set of ends thereof into a water exit chamber 48 formed inside the housing 22 on a second opposite side thereof. The exit chamber 48 communicates with an outlet fitting 50 (FIG. 2) coupled to the housing 22. A hose (not illustrated) connected to the second fitting 50 conveys the water back to the source. It will be understood by those skilled in the art that during cardiac surgery, water is pumped through the blood oxygenator 20 in a closed loop. The loop includes temperature regulating devices to accurately maintain the temperature of the patient's blood at a predetermined level that is typically below normal body temperature. The temperature of the blood can be monitored by a circuit (not illustrated) that includes a thermister or other temperature sensing device (not illustrated) mounted inside an optional thermometer probe fitting (not illustrated) in the side of the housing 22.

The oxygenator fiber bundles 28–32 (FIG. 9) are advantageously constructed to optimize the blood oxygenation function. Each oxygenator fiber is made of a micro-porous polymer material as is well known in the art. The microscopic sized pores in the walls of the hollow fibers permit carbon dioxide from the blood surrounding the outside of the fibers to diffuse into the gas mixture inside of the hollow fibers. Similarly, oxygen from the gas mixture inside the hollow fibers can diffuse through the microscopic pores into the blood surrounding the outside of the fibers.

Preferably the oxygenator fibers are provided in the form of a continuous long web or mat 52 of mico-conduit wrapping material in which the fibers are held together by a thin, flexible, horizontally extending woven interconnect (not illustrated). Similar material is commercially available from Mitsubishi Rayon, Co., Ltd. under the designation HFE430-1 Hollow Fiber. This material uses polyethylene fibers. Another suitable material is commercially available from Hoechst Celanese Corporation under the designation Heat Exchanger Fiber Mat. This material uses polypropylene fibers. Each of the fiber bundles 28–32 is made by fan folding a long segment of the mat 52 as illustrated in FIG. 8 so that the open ends of the oxygenator fibers terminate on opposite ends of the resulting box-shaped bundle. The opposite ends of the bundles 28–32 are supported by horizontal racks or shelves 53 (FIG. 10) of the frame 34. Preferably the individual oxygenator fibers extend at an oblique angle relative to the transverse direction as seen in FIG. 8. This angle is preferably between one and fifteen degrees relative to the transverse direction or lateral dimension of the mat 52. This oblique angle can be formed during the production of the mat 52, or by flexing or displacing one side edge of the mat longitudinally relative to the other side edge of the mat. Together with oxygenator bundles 28–32 provide thousands of oxygenator fibers to oxygenate the blood flowing through the blood oxygenator 20.

Figure 4:
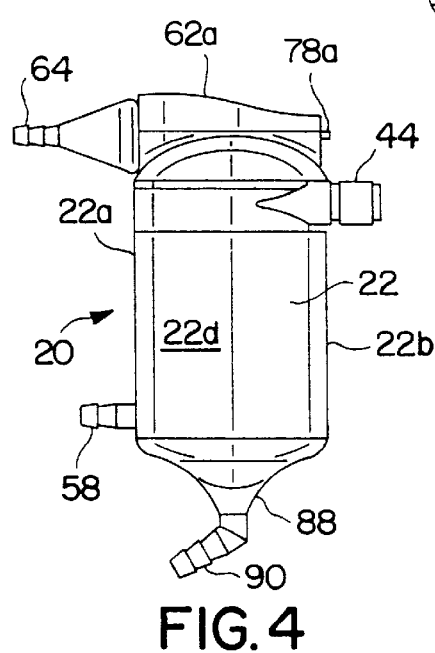
FIG. 4 is a side elevation view of the blood oxygenator of FIG. 1 taken from the right side of FIG. 3.
Figure 11:
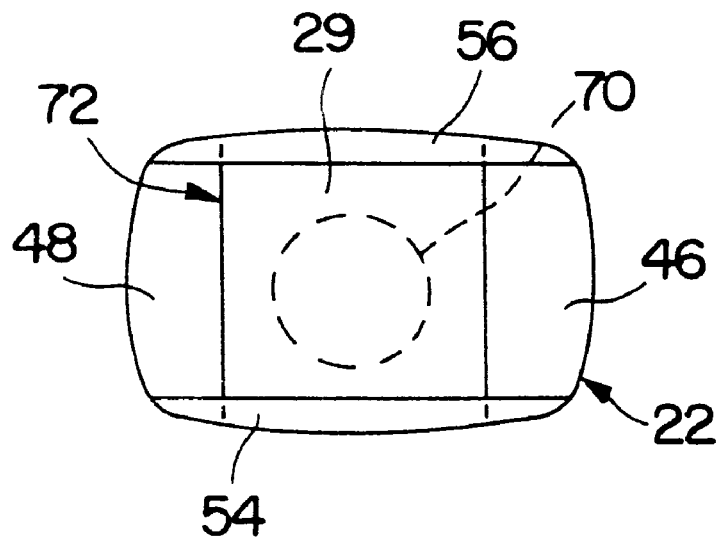
FIG. 11 is a diagrammatic horizontal cross-sectional view of the blood oxygenator of FIG. 1 taken along line 11—11 of FIG. 6.

A first set of open ends of the oxygenator fibers in the bundles 28–32 communicate with a gas entry chamber 54 (FIG. 11) formed inside the housing 22 on a front side thereof. A second opposite set of open ends of the oxygenator fibers in the bundles 28–32 communicate with a gas exit chamber 56 formed inside the housing 22 on a rear side thereof. A barbed gas inlet nozzle 58 (FIGS. 1, 4 and 6) is coupled to the entry chamber 54 for directing an oxygen-rich gas mixture from a source through a hose (not illustrated). This oxygen-rich gas mixture flows into to the first set of ends of the oxygenator fibers and through the fibers. As blood flows through the oxygenator fiber bundles 28–32 around the exterior surfaces of its individual oxygenator fibers, oxygen permeates through the fiber walls into the blood. At the same time, carbon dioxide in the blood permeates in the other direction through the walls of the fibers into the gas mixture flowing through the tubes. The carbon dioxide laden gas mixture exits the fibers from a second set of ends thereof into the gas exit chamber 56. A barbed gas outlet nozzle 60 (FIG. 2) is coupled to the gas exit chamber 56 for directing the gas mixture flowing out of the second set of ends of the oxygenator fibers to another hose (not illustrated) connected to the outlet nozzle 60.

Figure 2:
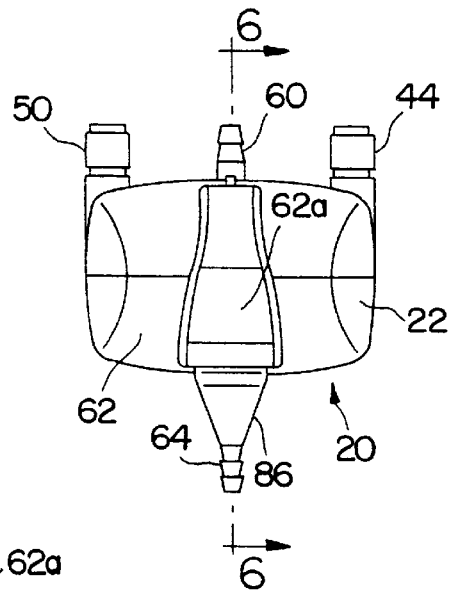
FIG. 2 is a top plan view of the blood oxygenator of FIG. 1.

The fibers of the oxygenator bundles 28–32 are microporous. Carbon dioxide from the blood surrounding the fibers diffuses through the walls of the fibers into the gas mixture. Similarly, oxygen from the gas mixture inside the fibers of the bundles 28–32 diffuses through the micro-pores into the blood. The gas mixture now having an elevated carbon dioxide content leaves the fibers and flows into the exit chamber 56 (FIG. 11) and then is vented therefrom via the gas mixture outlet nozzle 60 (FIG. 2). This gas mixture now has a lowered oxygen content.

Figure 3:
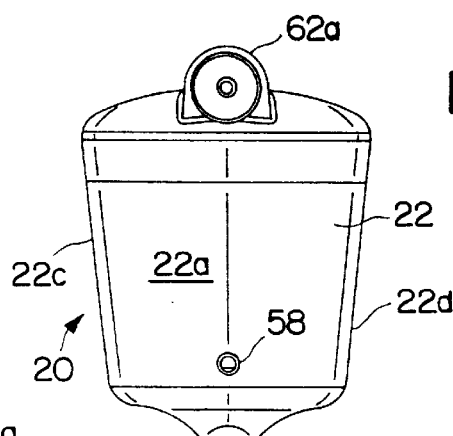
FIG. 3 is a front elevation view of the blood oxygenator of FIG. 1.

The generally rectangular housing 22 has parallel front and back side walls 22a and 22b (FIG. 4) and tapered, downwardly converging left and right side walls 22c and 22d (FIG. 3). The eight corners of the generally rectangular housing 22 are rounded. The chambers 46, 48, 54 and 56 are thus formed on four adjacent sides of the housing 22.

Referring again to FIG. 1, the upper end of the housing 22 is formed to provide a blood inlet manifold generally designated by the reference numeral 62. The blood inlet manifold 62 is preferably injection molded as a single unitary piece of plastic which is glued to the sidewalls 22a, 22b, 22c and 22d of the housing 22. The blood inlet manifold 62 includes a barbed blood inlet nozzle 64 for delivering blood from a blood flow line in the form of a tube 66 (FIG. 13) to the upper end of the housing 22. The blood initially flows horizontally into the housing 22 but is directed downwardly by a gently curved inner wall surface 68 (FIG. 6) of the blood inlet manifold 62. The inner wall surface 68 is curved to provide a generally spherical-shaped inlet to the interior of the housing 22. This allows the blood to flow smoothly through an approximately right angle turn into a central cylindrical region 70 (FIGS. 11 and 12) of the interior of the housing 22. This central region 70 which serves as the blood flow path is indicated by the phantom line circles in FIGS. 11 and 12. The central region 70 is defined by a block 72 of cured potting compound formed over the skeletal framework 34, heat exchanger conduit groups 24–27 and oxygenator fiber bundles 28–32. The block 72 of potting compound has a cylindrical interior surface defining the blood flow path and a plurality of generally planar exterior surfaces substantially co-planar with the open ends of the conduits and oxygenator fibers. The blood flows in a longitudinal or vertical direction downwardly between the chambers 46, 48, 54 and 56 past, and in contact with, the outside of the segments of the heat exchanger conduits and the oxygenator fibers which traverse the cylindrical central region 70.

The block 72 of potting compound (FIGS. 11 and 12) may be formed in the following manner. After the heat exchanger conduit groups 24–27 and the oxygenator fiber bundles 28–32 (FIG. 9) have been installed into the skeletal framework 34 (FIG. 10) the forward and rearward vertical sides of the framework adjacent the shelves 53 are encased. Uncured liquid potting compound such as polyurethane is then introduced into the framework 34 while the framework 34 is being spun at approximately seventeen hundred RPM about a central vertical axis of the region 70. The skeletal framework 34 includes top and bottom panels such as 74 having circular cutouts 75 that coincide with the perimeter of the central region 70. Once the potting compound has cured the framework 34 is unloaded from its spinning fixture and the encasing members on the two sides of the framework 34 are removed. The ends of the conduits and oxygenator fibers are still open so that they can communicate with corresponding ones of the chambers 46, 48, 54 and 56.

The blood inlet manifold 62 (FIG. 6) is formed with a flared portion 62a that houses an axial flow pump 36 including a bladed impeller 76 (FIGS. 6 and 7). The impeller 76 is mounted to the forward end of a horizontal shaft 78 (FIG. 6) that is journaled in forward and aft bearings 80 and 82 mounted inside the flared portion 62a of the blood inlet manifold 62. The bearings 82 are sealed in fluid-tight fashion so that a flattened rear end 78a (FIGS. 4 and 6) of the shaft 78 can extend outside the blood inlet manifold 62 for releasable mechanical connection to an external motor shown diagrammatically at 84 in FIG. 6. The rear end of the barbed blood inlet nozzle 64 is connected to a generally conical-shaped intake 86 which feeds the blood to the impeller 76.

The use of an internal pump in the blood oxygenator 20 further reduces the amount of blood otherwise needed in a perfusion circuit if an external pump were utilized. For example, conventional heart-lung perfusion circuits often utilize peristaltic pumps which require that a substantial length of tubing that is progressively squeezed by the pump be filled with blood.

Figure 5:
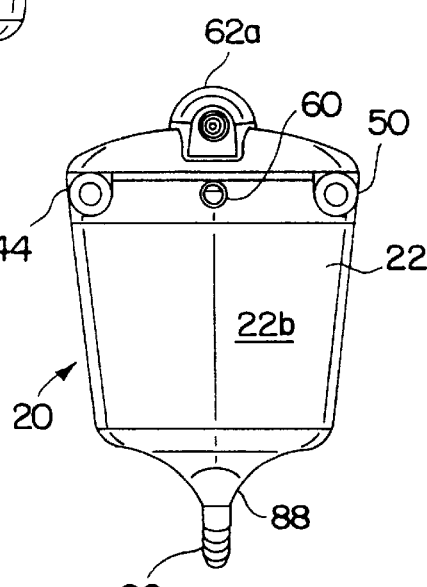
FIG. 5 is a rear elevation view of the blood oxygenator of FIG. 1.

Referring to FIGS. 5 and 6, the lower end of the housing 22 is formed to provide a blood outlet manifold generally designated by the reference numeral 88. The blood outlet manifold 88 includes a barbed blood outlet nozzle 90 for delivering blood to a return blood flow line in the form of a tube 92 (FIG. 13) to the arterial cannula 38. The blood outlet manifold 88 is preferably injection molded as a single unitary piece of plastic which is glued to the sidewalls 22a, 22b, 22c and 22d of the housing 22. It includes a gradually tapered conical portion 88a (FIG. 6) having slightly convex curved inner wall surfaces 94.

Referring to FIG. 10, the framework 34 has four rectangular peripheral edges such as 96, one on each of the four sides of the framework 34. These edges are glued or otherwise bonded to mating rectangular peripheral flanges 97 (FIG. 7) formed on the interior surfaces of the sidewalls 22a, 22b, 22c and 22d of the housing 22. The frame 34 is preferably glued to the sidewalls 22a, 22b, 22c and 22d before the inlet and outlet manifolds 62 and 88 are glued to the upper and lower ends of the housing 22. The mating peripheral edges 96 and peripheral flanges 97, along with the block 72 of cured potting compound define the four outer chambers 46, 48, 54 and 56 (FIGS. 11 and 12) on the sides of the housing 22. These four chambers feed and collect water and gas from the conduit groups 24–27 and fiber bundles 28–32, respectively.

It will thus be understood that the combination of the block 72 of potting compound and the gluing of the peripheral edges 96 to the flanges 97 of the housing 22 provides a means for hermetically sealing the three flow paths from each other as well as the ambient environment. The present invention advantageously longitudinally intersperses the heat exchanger conduits and oxygenator fibers which extend transversely in a criss-cross fashion and provides a blood flow path longitudinally through the conduits and fibers. This allows the same physical space to serve both the heat exchange functions and blood oxygenation functions, thus minimizing blood priming volume. Prior art blood oxygenators have typically separated the heat exchange and blood oxygenation functions into dedicated structures which have been longitudinally or concentrically spaced apart, for example.

Except for the heat exchanger conduit groups 24–27, the oxygenator fiber bundles 28–32, and the block 72 of potting compound, the remainder of the structures illustrated and described herein are preferably injection molded of clear polycarbonate plastic. The clear plastic allows the physician to visually confirm that the oxygenator is filled with blood. Suitable plastics are commercially available under the designations BAYER Makrolon and General Electric LEXAN HAP2R-1112. Separately molded plastic components may be assembled and permanently affixed to each other with a suitable non-toxic ultraviolet (UV) curable adhesive or by other suitable means such as sonic welding.

FIG. 13 is a schematic diagram of a specially modified perfusion circuit incorporating the blood oxygenator 20 of the present invention. An outlet cannula 98 is implanted in a patient's clinically appropriate access vessel such as a vein. The outgoing blood flow line 66 connects the outlet cannula 98 and the inlet of the pump 36 on the inlet side of the blood oxygenator 20. Blood is pumped downwardly through the central region 70 of the blood oxygenator 20 and then through the return blood flow line 92 to the inlet cannula 38 implanted in a patient's clinically appropriate inlet vessel such as an artery. A blood reservoir 100 in the usual form of a collapsible plastic bag has an inlet and an outlet at the bottom thereof. A parallel blood flow line 102 including a first adjustable flow restricting device 104 is connected between the outgoing blood flow line 66 and an outlet of the blood reservoir 100. The adjustable flow restricting device 104 may take the form of a conventional roller clamp. Another parallel blood flow line 106 including a second adjustable flow restricting device 108 is connected between the return blood flow line 92 and the inlet of the blood reservoir 100. A reservoir 110, for holding a suitable bio-compatible buffering fluid such as saline solution, is connected to an auxiliary fluid flow line 112. The auxiliary fluid flow line 112 includes a third adjustable flow restricting device 114 and connects the fluid reservoir 110 and the parallel blood flow line 106. The blood reservoir 100 has a pair of vent ports 116 and 118 at the top thereof. These vent ports include fourth and fifth adjustable flow restricting devices 120 and 122.

The modified perfusion circuit of FIG. 13 decreases the likelihood of tissue damage at the location of the outlet cannula 98. The blood reservoir 100 acts as an accumulator in that it can supply blood to the oxygenator 20 if there is insufficient flow from the outlet cannula 98. This alleviates negative pressure at the outlet cannula 98 and lessens the likelihood of tissue damage. The flow restricting device 104 can be adjusted to ensure that blood will be drawn by the pump 36 from the blood reservoir 100 in the event that the outlet cannula 98 is partially blocked or obstructed by the patient's vein or other tissue. The flow restricting device 108 can be adjusted to ensure the appropriate amount of return flow to the blood reservoir 100. The flow restricting device 114 can be adjusted to replenish the blood reservoir 100 if it has been subjected to excessive drawn down.

Having described a blood oxygenator incorporating a preferred embodiment of the present invention, and a specially modified perfusion circuit incorporating the same, it will occur to those of ordinary skill in the art that the preferred embodiment can be modified in both arrangement and detail while still embodying said invention. For example, the blood oxygenator 20 need not include its own internal pump. Accordingly, the protection afforded the subject invention should only be limited in accordance with the following claims.

What is claimed is:

1. A blood oxygenator, comprising:

a housing defining a hollow interior;

a heat exchanger including a plurality of conduits extending in a transverse direction across the interior of the housing, the heat exchanger conduits being arranged in a plurality of discrete groups spaced apart in a longitudinal direction within the housing;

a plurality of oxygenator fibers extending in the transverse direction across the interior of the housing, the oxygenator fibers being arranged in a plurality of discrete bundles spaced apart in the longitudinal direction within the housing, the oxygenator fiber bundles being interspersed with the heat exchanger conduit groups; and means for providing hermetic seals between a plurality of ends of the heat exchanger conduits, a plurality of ends of the oxygenator fibers and a plurality of inner surfaces of the housing to define a heat transfer fluid flow path extending through the heat exchanger conduits, a blood flow path extending in a longitudinal direction around the heat exchanger conduits and the oxygenator fibers, and a gas mixture flow path extending through the oxygenator fibers.

2. A blood oxygenator according to claim 1 wherein the conduits of the heat exchanger each comprise a metal tube.

3. A blood oxygenator according to claim 1 wherein the housing is generally rectangular.

4. A blood oxygenator according to claim 1 wherein the seal means defines a chamber on each of four adjacent sides of the generally rectangular housing.

5. A blood oxygenator according to claim 1 wherein the seal means includes a potting compound.

6. A blood oxygenator according to claim 1 and further comprising a pump mounted inside a portion of the housing for propelling blood through the blood flow path.

7. A blood oxygenator according to claim 6 wherein the pump is an axial flow pump mounted adjacent a blood inlet manifold forming an end of the housing.

8. A blood oxygenator according to claim 1 and further comprising a framework for supporting the heat exchanger conduit groups and the oxygenator fiber bundles.

9. A blood oxygenator according to claim 8 wherein the seal means includes a block of potting compound formed over the framework, heat exchanger conduit groups and oxygenator fiber bundles, the block of potting compound having a cylindrical interior surface defining the blood flow.

10. A blood oxygenator according to claim 1 wherein each oxygenator fiber bundle is made of fan folded mat of a plurality of generally parallel oxygenator fibers.

11. A blood oxygenator, comprising:

a generally rectangular housing defining a hollow interior;

a heat exchanger including a plurality of conduits extending in a transverse direction across the interior of the housing;

a plurality of oxygenator fibers extending in the transverse direction across the interior of the housing;

means for hermetically sealing a plurality of ends of the heat exchanger conduits and a plurality of ends of the oxygenator fibers to define a heat transfer fluid flow path through the heat exchanger conduits, a blood flow path extending in a longitudinal direction around the heat exchanger conduits and the oxygenator fibers, and a gas mixture flow path through the oxygenator fibers, the sealing means defining a heat transfer fluid entry chamber on a first side of the housing, a heat transfer fluid exit chamber on a second side of the housing, a gas entry chamber on a third side of the housing, and a gas exit chamber on a fourth side of the housing;

a heat transfer fluid inlet fitting communicating with an interior of the heat transfer fluid entry chamber of the housing;

a heat transfer fluid outlet fitting communicating with an interior of the heat transfer fluid exit chamber of the housing;

a blood inlet manifold forming a part of the housing for delivering blood from a first tube to a first end of the housing so that the blood will flow through a central region of the interior of the housing defined by the sealing means in a generally longitudinal direction between the chambers, around the heat exchanger conduits and around the oxygenator fibers;

a blood outlet manifold forming a part of the housing for delivering blood from a second end of the housing to a second tube after it has flowed through the central region of the housing around the heat exchanger conduits and around the oxygenator fibers;

a gas inlet nozzle coupled to the gas entry chamber for directing the gas mixture from a first hose to the first ends of the oxygenator fibers so that the gas mixture flows therethrough; and a gas outlet nozzle coupled to the gas exit chamber for directing the gas mixture flowing out of the second ends of the oxygenator fibers to a second hose.

12. A blood oxygenator according to claim 11 wherein the conduits of the heat exchanger each comprise a metal tube.

13. A blood oxygenator according to claim 11 wherein the sealing means includes a cured potting compound.

14. A blood oxygenator according to claim 11 and further comprising a pump mounted inside a portion of the housing for propelling blood through the central region of the interior of the housing.

15. A blood oxygenator according to claim 14 wherein the pump is mounted adjacent the blood inlet manifold and the blood inlet manifold has a curved inner wall surface for redirecting the blood flow through approximately a right angle turn.

16. A blood oxygenator according to claim 11 wherein the heat exchanger conduits are contained within a plurality of discrete groups spaced apart in the longitudinal direction and the oxygenator fibers are contained within a plurality of discrete bundles spaced apart in the longitudinal direction, the oxygenator fiber bundles be interspersed with the conduit groups.

17. A blood oxygenator according to claim 16 wherein the oxygenator fibers of each bundle are made of a fan folded mat of a plurality of generally parallel oxygenator fibers.

18. A blood oxygenator according to claim 16 and further comprising a frame mounted inside the housing for supporting the groups of heat exchanger conduits and oxygenator fiber bundles.

19. A blood oxygenator according to claim 18 wherein the sealing means includes a rectangular block of cured potting compound formed around the frame and having a cylindrical interior surface defining the central region of the interior of the housing through which the blood flows, and a plurality of peripheral edges on the framework are bonded to a plurality of inwardly projecting flanges of the housing to define the chambers.

* * * * *